(12) United States Patent
Schwartz et al.

(10) Patent No.: US 8,702,649 B2
(45) Date of Patent: Apr. 22, 2014

(54) MULTIPLE LUMEN DIFFUSION CATHETER

(75) Inventors: Robert S. Schwartz, Inver Grove Heights, MN (US); Robert A. Van Tassel, Excelsior, MN (US); Eugene A. Gelblum, Pittsburgh, PA (US); Alan D. Hirschman, Glenshaw, PA (US); John F. Kalafut, Pittsburgh, PA (US); David M. Reilly, Pittsburgh, PA (US); Frederick W. Trombley, III, Gibsonia, PA (US); Arthur E. Uber, III, Pittsburgh, PA (US)

(73) Assignee: Bayer Medical Care Inc., Indianola, PA (US)

(*) Notice: Subject to any disclaimer, the term of this patent is extended or adjusted under 35 U.S.C. 154(b) by 1072 days.

(21) Appl. No.: 12/515,981

(22) PCT Filed: Nov. 28, 2007

(86) PCT No.: PCT/US2007/085736
§ 371 (c)(1),
(2), (4) Date: Dec. 2, 2009

(87) PCT Pub. No.: WO2008/067362
PCT Pub. Date: Jun. 5, 2008

(65) Prior Publication Data
US 2010/0174183 A1 Jul. 8, 2010

Related U.S. Application Data

(60) Provisional application No. 60/867,550, filed on Nov. 28, 2006.

(51) Int. Cl.
*A61M 29/00* (2006.01)

(52) U.S. Cl.
USPC ............... 604/102.02; 604/96.01; 604/102.01

(58) Field of Classification Search
USPC ............. 604/96.01, 102.01–102.03, 104, 523
See application file for complete search history.

(56) References Cited

U.S. PATENT DOCUMENTS

| | | | |
|---|---|---|---|
| 5,290,263 A | | 3/1994 | Wigness et al. |
| 5,382,238 A | * | 1/1995 | Abrahamson et al. ... 604/170.01 |
| 5,554,114 A | | 9/1996 | Wallace et al. |
| 5,840,066 A | | 11/1998 | Matsuda et al. |
| 6,079,449 A | | 6/2000 | Gerber |
| 6,754,521 B2 | | 6/2004 | Prince |
| 6,811,542 B2 | | 11/2004 | Liska et al. |
| 6,855,132 B2 | | 2/2005 | VanTassel |
| 6,969,373 B2 | | 11/2005 | Schwartz |
| 7,415,759 B2 | | 8/2008 | Vischer |
| 2002/0016566 A1 | * | 2/2002 | Bertolero et al. ........ 604/102.03 |
| 2002/0069023 A1 | | 6/2002 | Shapiro et al. |
| 2002/0198432 A1 | | 12/2002 | Stiger et al. |
| 2003/0153898 A1 | | 8/2003 | Schon et al. |

(Continued)

OTHER PUBLICATIONS

International Search Report from Corresponding International Patent Application PCT/US07/85736.

*Primary Examiner* — Emily Schmidt
(74) *Attorney, Agent, or Firm* — David Schramm

(57) ABSTRACT

A method and device for the simultaneous or sequential introduction of multiple fluids into the bloodstream including a multiple lumen catheter with corresponding multiple hole sets. By introducing a second fluid such as saline, the concentration and bolus of a first fluid, such as a contrast agent, can be controlled and optimized.

20 Claims, 9 Drawing Sheets

(56) References Cited

U.S. PATENT DOCUMENTS

| | | |
|---|---|---|
| 2004/0220547 A1* | 11/2004 | Heruth et al. ............... 604/523 |
| 2005/0277870 A1 | 12/2005 | Pecor |
| 2006/0142703 A1 | 6/2006 | Carter et al. |
| 2008/0300573 A1* | 12/2008 | Consigny et al. ............ 604/509 |

* cited by examiner

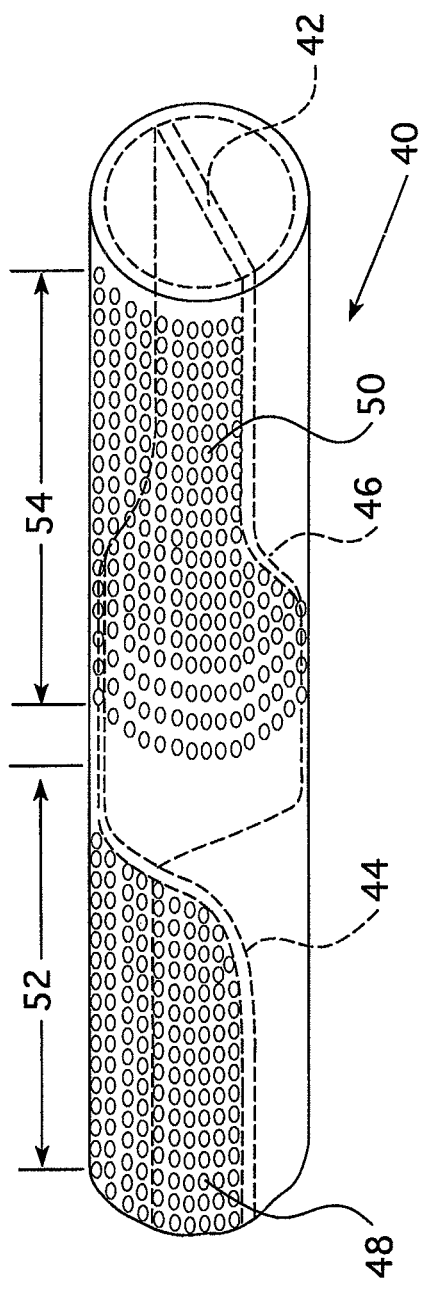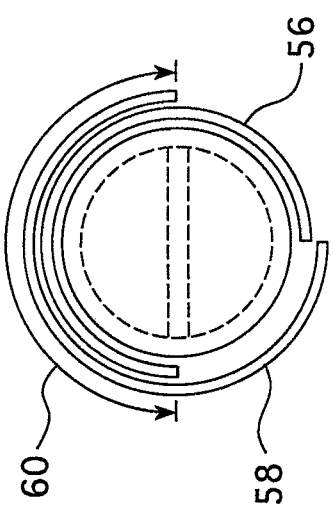
FIG. 3
FIG. 3a

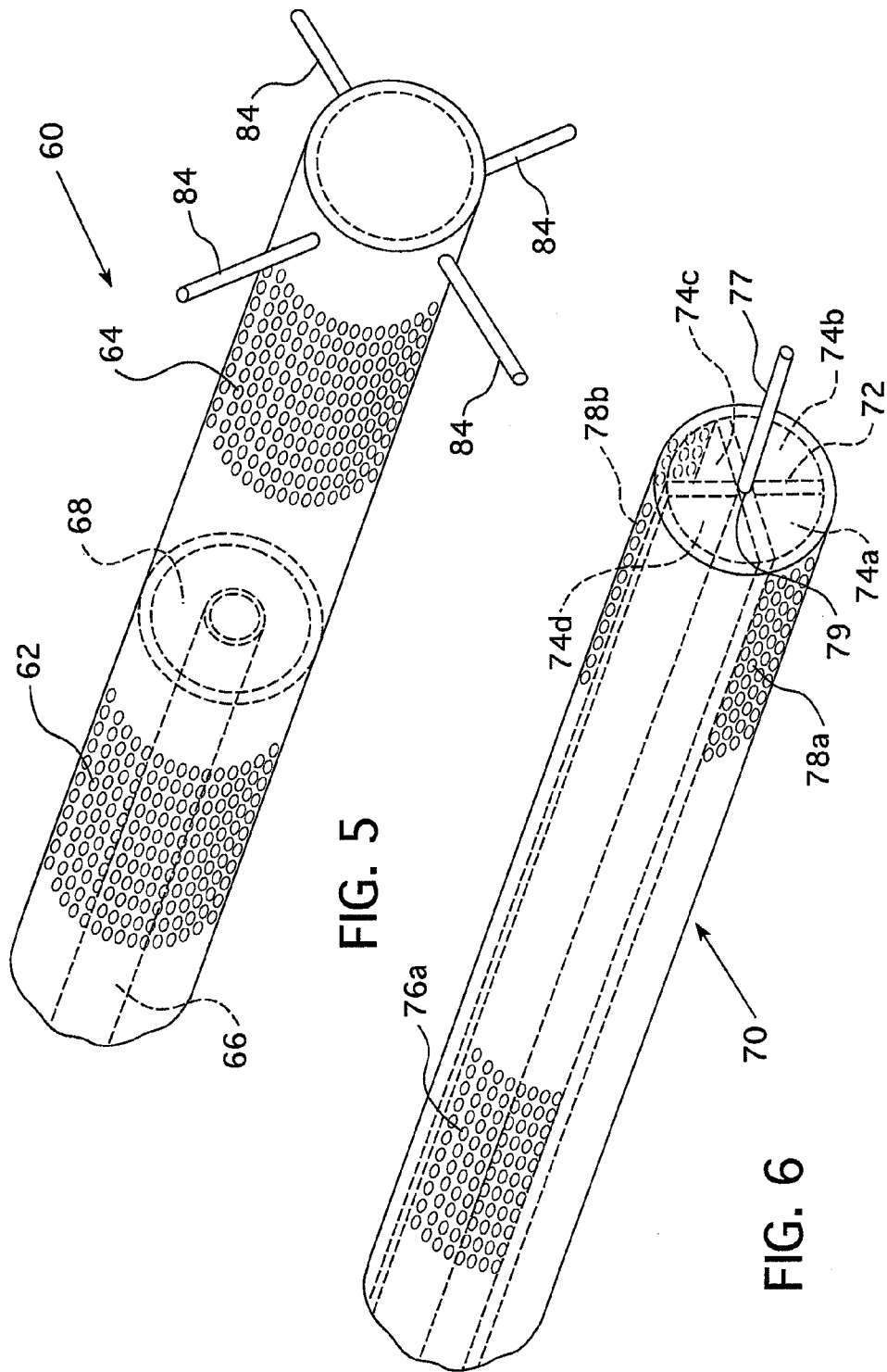

MULTIPLE LUMEN DIFFUSION CATHETER

RELATED APPLICATIONS

This application claims priority to U.S. Application Ser. No. 60/867,550, entitled MULTIPLE LUMEN DIFFUSION CATHETER, filed on Nov. 28, 2006 by Schwartz, et al., the entirety of which is incorporated herein by reference.

FIELD OF THE INVENTION

The present invention relates to a specialized catheter for insertion into an artery, vein, or other body structure, with principal use for contrast injection during an X-Ray, MRI, CT, CTA or other imaging or therapeutic procedure. Because it may be made for arterial application, or because of its arterial or venous concentrating capability, the catheter of the invention decreases contrast dose, making it ideal for use in treatment or diagnosis of diabetic renal disease or other renal dysfunction that mandates reduction in the dosage of contrast.

BACKGROUND OF THE INVENTION

Internal imaging is often enhanced through the use of injected imaging agents that allow an imaging technique (MRI, CTA, x-ray, ultrasound, etc.) to provide a brighter, clearer image of one or more anatomic structures. Imaging agents are formulated for a particular type of imaging technology and are used to better detect and differentiate the targeted vessels or other tissues from surrounding structures, and particularly so when compared to images of such tissues acquired without the use of such contrast agents.

Many contrast agents are directed toward imaging of the vasculature system. These agents are injected into the blood stream, either by artery or vein, and delineate the presence or absence of blood in the human vasculature. This type of imaging presents problems not encountered during other types of internal imaging, such as those employed in orthopedic studies, where a simple needle is used to inject contrast agent into a static joint socket or the like.

For example, vascular imaging presents the added difficulty of capturing the image of a moving target, either moving contrast agent or moving body structures like the heart, for example. Because the imaging agent is injected directly into the flow of the blood stream, the agent is immediately carried away and mixed with the blood, thereby weakening the contrast concentration it provides. Hence, the agent is typically delivered through a long catheter threaded through the vasculature to a location proximate the target area. Delivery catheters typically have an open end from which the agent is injected. Because the blood is flowing in the same direction the agent is expelled from the catheter, the agent is carried away quickly, necessitating the injection of a large volume of agent in order to achieve the desired results. Alternatively, imaging sometimes involves injection of agents against the blood flow. In this situation, the agent is similarly carried away.

Some catheters attempt to mitigate this effect by providing openings in the sides of the catheter rather than just at the end. Quite often, however, these side openings are blocked because the catheter is resting along an inside wall of the vessel lumen. This can result in a diminished contrast effect and, due to the increased fluid pressure through the holes that are not blocked, trauma to the vessel. Furthermore, because of the high volume of agent being injected, the exit holes from the catheter are typically large, thereby reducing the amount of force necessary to inject the agent at a high flow rate. The large volume of agent being pushed through these holes adds to the potential vessel trauma in two ways. First, even if the catheter holes are not blocked on one side by the vessel walls, the jet effect of the high volume of contrast agent injection rapidly exiting the holes may injure tissue as the fluid streams impact the vessel walls. Second, the jet effect may cause the catheter to move or whip during injection, damaging tissue as the catheter itself impinges on the vessel walls.

One example of a needle or catheter that incorporates holes along its sides is shown and described in U.S. Pat. No. 6,855,132, issued Feb. 15, 2005 to Van Tassel, et al., entitled Apparatus With Weeping Tip And Method Of Use, and in U.S. Pat. No. 6,969,373, issued Nov. 29, 2005 to Schwartz, et al., entitled Syringe System. Both of these references are incorporated by reference herein. Some of the embodiments of catheters discussed in these references mitigate jet effect by providing large numbers of smaller holes, thereby reducing the fluid velocity through any given hole. However, the embodiments of catheters in these references do not address retrograde flow problems associated with ejecting fluid through side holes.

Retrograde flow occurs occasionally when ejecting contrast agent at high velocities through catheters with side holes. If the blood stream flow rate is significantly slower than the injectate flow rate, it is possible to encounter contrast agent traveling upstream. This diminishes the definition of the bolus image. During applications where agent is used for opacification of the heart, injectate entering the venous side of the heart has to travel through the pulmonary system before entering the arterial side of the heart. The pulmonary system significantly diffuses the bolus, making imaging of the arterial side more difficult. Hence, beginning with a highly concentrated, well defined bolus of contrast agent becomes paramount.

SUMMARY OF THE INVENTION

The present invention overcomes many of the problems in the art by providing a catheter tip that is self-centering within a lumen and includes a plurality of discharge hole sets that are constructed and arranged to create bolus clouds, rather than a single jet bolus, of injectate. The bolus clouds, in contradistinction to an injectate stream from an end port of a catheter, are concentrated masses of injectate that maximize imaging while minimizing the amount of injectate necessary, providing atraumatic vascular injection. The cloud configuration concentrates contrast agent around the catheter, a phenomenon that does not occur with end hole injection since the jet distributes contrast linearly along the vessel. The holes may be deployed according to a spatial/longitudinal gradient down the catheter to provide equal injection of contrast (or other injectate) volume per unit of catheter length. Hence, a bolus concentrator is formed as all exiting contrast in cloud form displaces blood retrograde and antegrade at the injection site. By controlling flow rate through the injection catheter, any bolus spatial length and concentration can be achieved. Such bolus concentration-time control is not obtainable using end-hole devices. The plurality of holes also permits excellent blood-agent mixing, if desired. The smaller nature of the holes create a pressure gradient that uses energy from the flowing injectate, and thus by decreasing energy causes less likelihood of injuring tissue, or whipping of the catheter.

Control over bolus length, concentration, and movement in retrograde and antegrade directions is significantly enhanced by providing catheters having multiple lumens and corresponding hole sets through which fluid exits the lumens. Hole sets emitting a non-agent fluid such as saline are used to influence the bolus cloud of holes emitting an agent. The saline hole sets may have different hydraulic impedance than the agent hole sets to allow differential fluid exit pressure from the saline hole sets compared to the agent hole sets.

Moreover, saline hole sets may be provided on either side of an agent hole set, so that pressure may be enhanced preferentially at either end of the agent hole set, thus keeping the agent bolus focused. Either of the saline clouds emitted from the saline hole sets may be diminished relative to the other such that the agent bolus is "pushed" in one direction or the other.

In one presently preferred embodiment, the invention provides a catheter for introducing more than one fluid into a fluid stream. The catheter includes a distal tip and a catheter body defining at least a first lumen and a second lumen. A first set of holes in the distal tip leads to the first lumen; and a second set of holes in the distal tip leads to the second lumen.

In another presently preferred embodiment, the invention provides a catheter having an elongated catheter body and a baffle. The elongate catheter body defines a lumen, and the baffle bifurcates the lumen into a first passage and a second passage. A first set of holes about a distal tip of the catheter leads to the first passage, and a second set of holes about the distal tip leads to the second passage.

In a related aspect, the invention provides a method of preventing retrograde flow. The method includes the steps of: introducing a first fluid into a lumen through which a native fluid is flowing; and introducing a second fluid upstream of the first fluid such that the first fluid is prevented from traveling upstream by the second fluid.

In another related aspect, the invention provides a method of opacifying a heart. The method includes the steps of: introducing a first bolus of contrast agent into the right side of the heart; and introducing a second fluid upstream of the contrast agent such that the second fluid prevents the contrast agent from traveling in an upstream direction. The method also includes the steps of: waiting while the first fluid travels through the pulmonary system; and introducing a second bolus of contrast agent into the right side of the heart.

BRIEF DESCRIPTION OF THE DRAWINGS

FIG. 3 is a perspective view of an embodiment of a catheter tip;

FIG. 3a is an end view of the catheter tip of FIG. 3 including graphics showing the spray coverage from hole sets formed therein;

FIG. 5 is a perspective view of an embodiment of a catheter tip;

FIG. 6 is a perspective view of an embodiment of a catheter tip;

DETAILED DESCRIPTION OF THE INVENTION

Multiple Lumen Design

Figure 1:
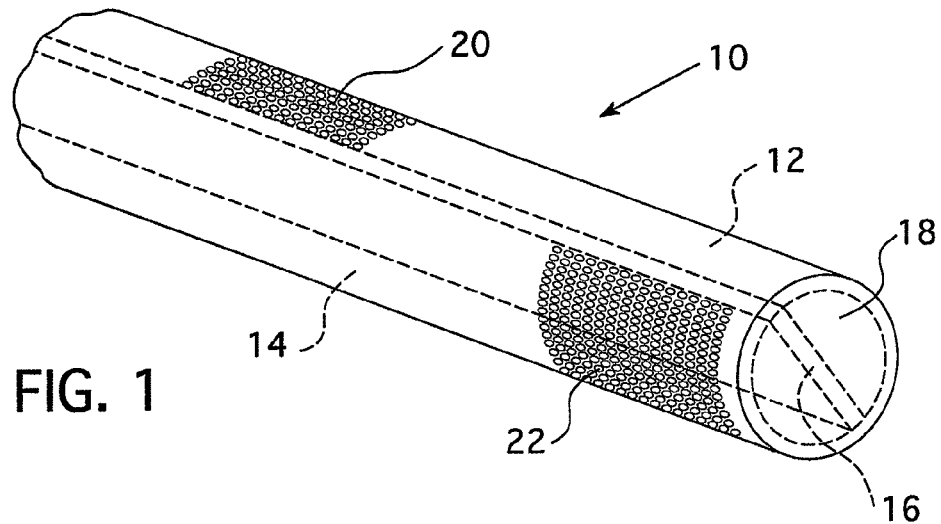
FIG. 1 is a perspective view of an embodiment of a catheter tip.

The various embodiments of the present invention include many innovative characteristics, each of which will be described in detail herein with the understanding that each of these characteristics may be used in combination with any or several of the other characteristics without departing from the spirit of the present invention. As such, one characteristic common to each of the various embodiments of the present invention is a multiple lumen design. For example, FIG. 1 shows an embodiment of a catheter 10 having a first lumen 12 and a second lumen 14. The catheter 10 may be a guiding catheter, microcatheter, balloon catheter, injection catheter, or any other catheter. The lumina 12 and 14 are separated by a baffle 16 that runs longitudinally through the center of the catheter 10, bifurcating the interior space of the catheter into the two lumina 12 and 14. The distal end 18 of the catheter 10 is preferably blocked, but may have a small hole to accommodate a guidewire (not shown in FIG. 1 but shown and described in FIG. 5 and below, respectively). Each of the lumina 12 and 14 are in fluid flow communication with the outside of the catheter 10 via hole sets 20 and 22, respectively. The hole set 20 is proximal relative to the more distal hole set 22. Preferably, as will be described in detail below, the proximal hole set 20 is used to inject a non-agent fluid, such as saline, while the distal hole set 22 is used to inject an agent, such as a contrast agent or medicament. Differential hydraulic impedance can be created longitudinally by manipulating the size of the holes, the number of holes, and the number of holes per unit area.

Figure 2:
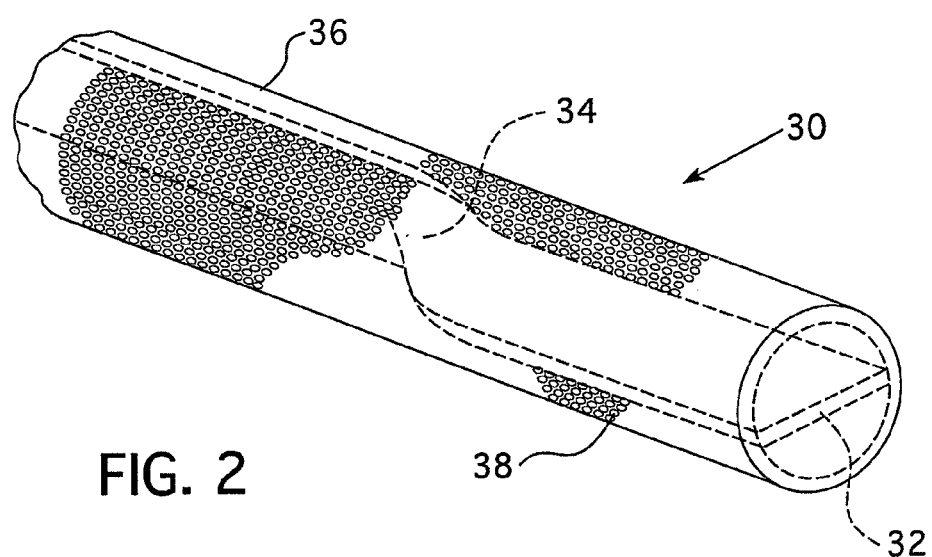
FIG. 2 is a perspective view of an embodiment of a catheter tip.
Figure 2A:
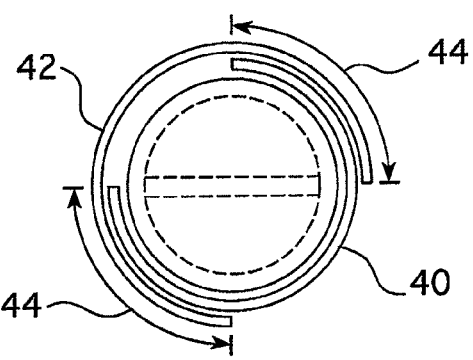
FIG. 2a is an end view of the catheter tip of FIG. 2 including graphics showing the spray coverage from hole sets formed therein.

Various embodiments of multiple lumen catheter designs are shown in FIGS. 1-6. The catheter 30 of FIG. 2 includes a baffle 32 that includes a 90 degree bend 34. The ninety degree bend 34, in conjunction with proximal hole set 36 and distal hole set 38, facilitates an injection pattern that includes a 270 degree arc 40 (see FIG. 2a) from the proximal hole set 36 and a 270 degree arc 42 from the distal hole set 38. The respective 270 degree arcs 40 and 42 result in a 180 degree total radial overlap 44. The 90 degree bend 34 could be formed by using a twisted baffle 32 in a straight catheter 30 or by heating and twisting both the catheter 30 and the baffle 32. If more overlap is desired, a 180 degree bend could be used or any other angle as is appreciated by one skilled in the art.

In order for the proximal and distal hole sets 36 and 38 to both follow the bend 34, a longitudinal coverage overlap results. Longitudinal overlap may be desired as the design lends itself to simultaneous injections of both saline and agent, such that the two liquids mix together after exiting the catheter. By allowing the liquids to mix, it is possible to dilute or control the concentration of the agent at the injection site rather than prior to injecting the fluids. Hence, changes in the concentration of the agent may be made during the injection.

For example, if the agent being injected is a contrast agent, an operator injecting the two fluids may adjust the contrast agent concentration while watching a monitor, thereby "fine tuning" the picture by changing the mixture of agent and saline.

If it is desired to create complete longitudinal spacing between the hole sets, a double bend may be used such as that shown in catheter 40 of FIG. 3. The catheter 40 has a baffle 42 which incorporates a first 90 degree bend 44 and a second 90 degree bend 46 spaced longitudinally from the first 90 degree bend 44. Corresponding to the 90 degree bends 44 and 46 are a proximal hole set 48 and a distal hole set 50. The proximal hole set 48 spans the first bend 44 and the distal hole set 50 spans the second bend 46. Arrows 52 and 54 show the approximate longitudinal coverages of the proximal hole set 48 and the distal hole set 50, respectively, and a longitudinal space therebetween.

FIG. 3a shows the radial coverage of each hole set and the overlap afforded by the first and second bends 44 and 46 in the baffle 42. The proximal hole set 48 has a 270 degree coverage arc 56 and the distal hole set 50 has a 270 degree coverage arc 58, resulting in complete 360 degree coverage with a 180 degree overlap 60.

Figure 4:
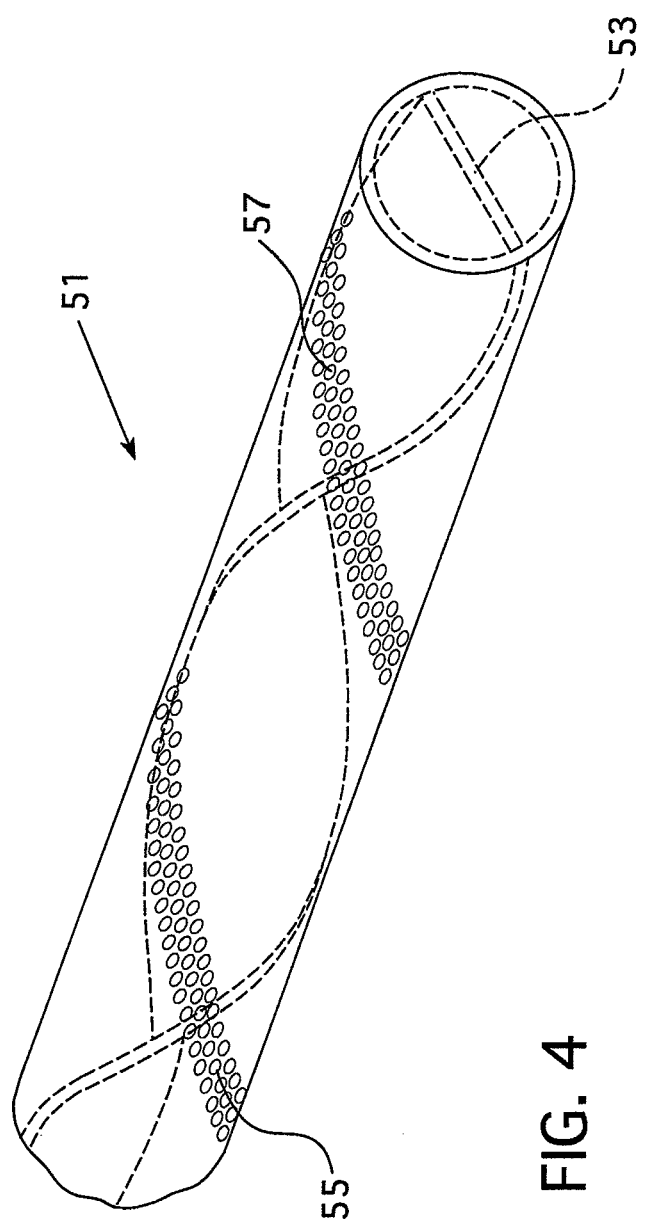
FIG. 4 is a perspective view of an embodiment of a catheter tip.

FIG. 4 shows a catheter 51 formed by taking a catheter, such as catheter 10 of FIG. 1, and heating it to a point where it can be twisted and cooled in order to form a catheter 51 with a twisted baffle 53. Alternatively, this baffle could be twisted through the extrusion manufacturing process by rotating the internal aspect of the extrusion die which forms the baffle. Through precise control, this twisted baffle could be applied to the entire catheter such as shown in FIG. 4 or periodically as described in FIGS. 2 and 3. Of course, any number of embodiments could be developed using this technique. A proximal hole set 55 and a distal hole set 57 are also twisted such that complete coverage is accomplished.

FIG. 5 shows a catheter 60 that includes a proximal hole set 62 and a distal hole set 64 that each have 360 degree coverage. Rather than incorporating a baffle that splits the interior of the catheter 60 into two or more lumina, an inner tube 66 runs concentrically through the interior lumen of the catheter 60. The inner tube 66 is hollow and ends at a radial baffle 68, which supports the distal end of the inner tube 66 and blocks the remaining luminal space of the catheter 60 surrounding the inner tube 66. The radial baffle 68 thus prevents fluid flowing around the outside of the inner tube 66 from exiting the distal hole set 64 and forces the fluid to exit through the proximal hole set 62.

The concentric lumen design of catheter 60 also results in a non-contrast agent having a higher pressure than the contrast agent. Since the inner tube 66 has a much smaller inner diameter than the catheter 60, and since the fluid path of the contrast agent begins in the inner tube 66 and then occupies the entire inner lumen of the catheter 60 as it exits the inner tube 66 after passing through the baffle 68, a pressure drop occurs. The non-contrast agent, however, flows through a space having a relatively constant cross-section. Hence, the non-contrast agent exiting the proximal hole set 62 will effectively prevent the contrast agent exiting the distal hole set 64 from traveling in an upstream direction. Forming a small hole in the distal end of the catheter 60 also makes this design ideally suited for following a guidewire.

FIG. 6 shows yet another embodiment of a multi-luminal design. The catheter 70 has a baffle 72 that divides its inner lumen 74 into four separate lumina 74a-d. This design provides the ability of providing two proximal hole sets 76a and 76b (76b not shown in the Figure) that span 90 degrees each and are located 180 degrees apart, giving an effective 360 degrees coverage in operation, and two distal hole sets 78a and 78b similarly configured. Additionally, as one skilled in the art will appreciate, this design lends itself to the introduction of four separate liquids through hole sets that may be arranged in a variety of longitudinal locations. If bends were to be incorporated into the baffle of this design, such as those shown in FIGS. 2 and 3, a 45 degree bend would accomplish the same coverage as a 90 degree bend in a design having two lumina instead of four.

The catheter 70 is also shown with a guidewire 77 protruding from a separate guidewire lumen 79 formed in the middle of the baffle 72. As with all of the features described herein, a guidewire, such as the guidewire 77, may be incorporated into any of the catheter designs herein described. Additionally, the guidewire 77, though shown slidably contained within guidewire lumen 79, may be permanently attached to the catheter, as would be ideally suited for a catheter having a tip with an extremely soft durometer. Though shown as being straight, the guidewire 77 may be curved at its distal end to assist in seeking a main channel of a vessel.

Figure 7:
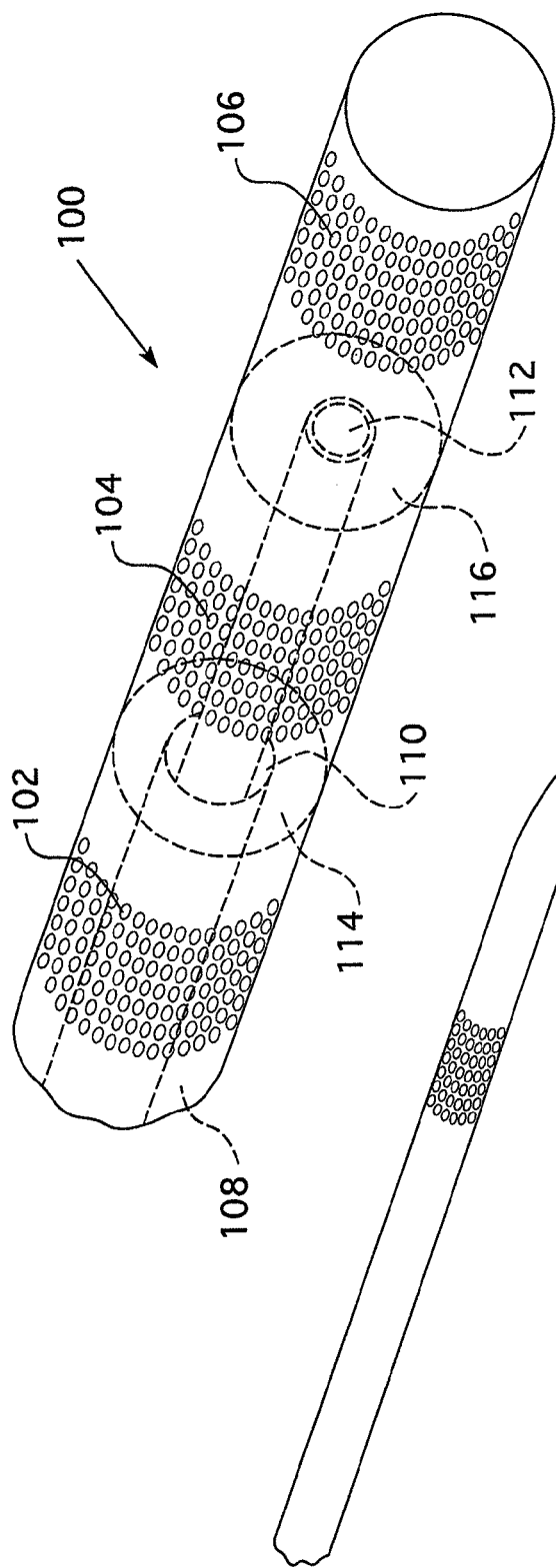
FIG. 7 is a perspective view of an embodiment of a catheter tip.

FIG. 7 shows a catheter 100 having a proximal hole set 102, a middle hole set 104 and a distal hole set 106 being fed by three concentric interior lumina 108, 110, and 112, respectively. The lumina are formed using the inner tubing previously described but could also be formed using the baffle design described above. Radial baffles 114 and 116 prevent fluid directed to each hole set from mixing until after exiting through the hole sets.

The three hole set design of catheter 100 is suited for creating a standing bolus of contrast agent or medicament. The proximal hole set 102 and the distal hole set 106 are fed a non-agent fluid, such as saline, while the middle hole set 104 is fed an agent, such as a contrast agent or medicament. By controlling the pressures of the proximal and distal hole sets 102 and 106, an agent bolus may be formed, virtually held in place, and then released in either a retrograde direction, by ceasing the injection of fluid through the proximal hole set 102, or in an antegrade direction, by ceasing the injection of fluid through the distal hole set 106.

Tips

Figure 8:
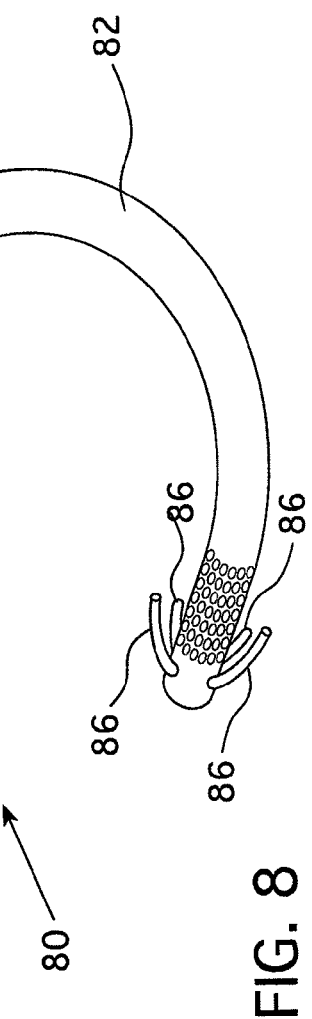
FIG. 8 is a perspective view of an embodiment of a catheter tip.

The catheter 80 shown in FIG. 8 has a distal tip with a curve 82. This curve may be used with any of the catheter designs described herein. The curve 82 is either pre-formed or created using an internal member (not shown) that generates the curve 82. This internal member could be a wire, a shaped-memory metal such as Nitinol, a spring, a polymer insert, or the like. The internal member could reside in the central lumen of the catheter 80 or could be isolated therefrom by incorporation into the catheter walls or providing a separate lumen therefor. The curve 82 is designed to fit the coronary sinus, entering either from the superior or inferior venae cavae. The curve 82 is gentle, thereby preventing trauma to native tissues.

Figure 9:
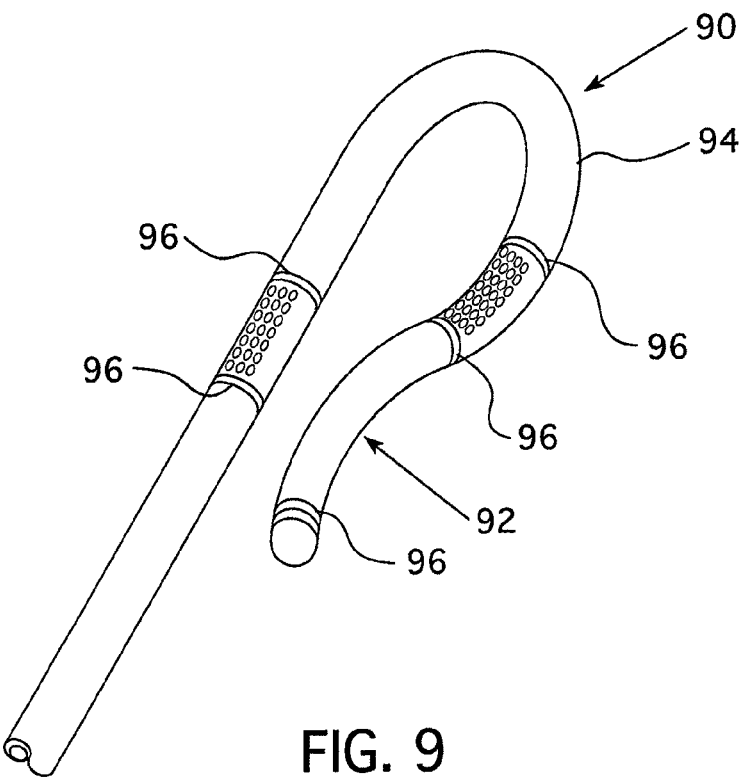
FIG. 9 is a perspective view of an embodiment of a catheter tip.

With or without a curve, any of the tips of the catheters described herein may have a differential durometer that permits a softer, more flexible distal tip. Navigating the venous structures with a catheter having such a tip can be accomplished by pushing the proximal end of the catheter, while allowing the soft tip to bend passively. A tip having a differential durometer is atraumatic to surrounding tissue. For example, FIG. 9 shows a catheter 90 having a tip 92 with a differential durometer. The tip 92 is significantly softer than a more proximal portion of the catheter 90. It can be seen that the catheter 90 loses most of its longitudinal stiffness at bend 94 and the distal remainder of the catheter 90 is limp, thereby causing the tip 92 to loop back on the rest of the catheter 90. When the tip 92 is placed in a venous lumen and looped as shown, the tip will expand, fluid is injected therethrough, and fills the space of the venous lumen.

The catheter tip 92 is also shown with a plurality of radiopaque marker bands 96. Marker bands may be incorporated on any of the catheters shown and described herein in any number or location. The marker bands 96 on tip 92 are located on either side of each hole set such that an operator is able to tell the locations thereof.

The various catheters described herein may including centering mechanisms that protrude from the tip and maintain the hole sets in the center of the native lumen, thereby preventing the hole sets from being blocked. These mechanisms may include radiating prominences such as fibers, springs, arms, and the like. The centering mechanisms, in addition to keeping the hole sets from being blocked by the native lumen walls, keep the device within the main channel of the native lumen and prevent the unintentional travel of the catheter down a side branch. Many examples of such devices are shown and described in PCT International Application No. PCT/US2006/000082 filed Jan. 3, 2006 to Schwartz et al., incorporated herein by reference in its entirety.

The catheter 60 shown in FIG. 5 illustrates an embodiment of a centering mechanism. The centering mechanism consists of four radiating arms 84 that "feel" the walls of a venous lumen and maintain the tip of a catheter in the center thereof. The catheter 80 of FIG. 8 shows another embodiment of a centering mechanism consisting of a plurality of rearward-angled arms 86, angled to allow easier forward advancement of the catheter 80.

Figure 10:
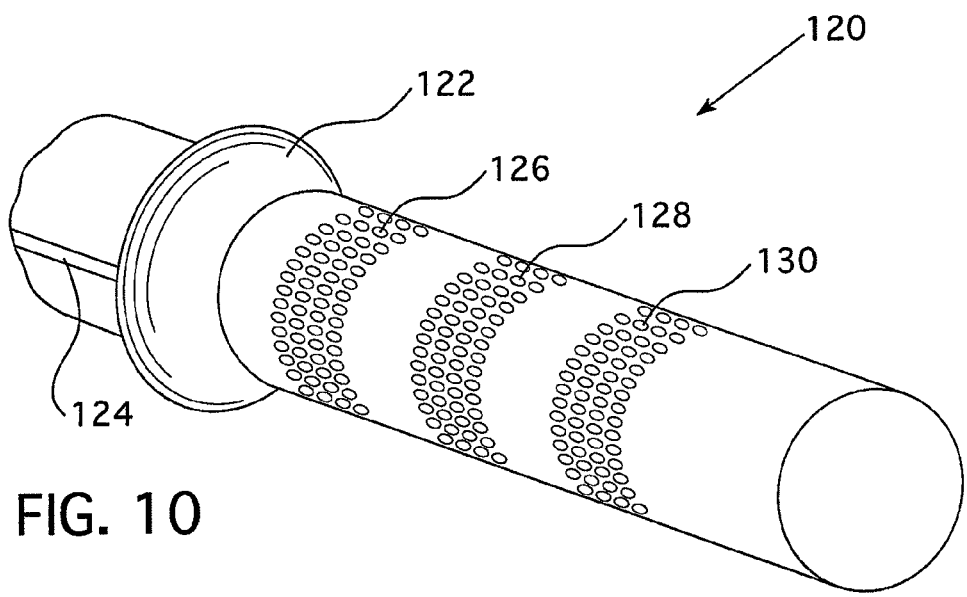
FIG. 10 is a perspective view of an embodiment of a catheter tip.

FIG. 10 shows a catheter tip 120 having an annular balloon 122 surrounding the catheter just proximal of three hole sets 126, 128 and 130. Each of the hole sets is in communication with a distinct lumen within the catheter for the purpose of controlling the composition of injected fluid. For example, hole set 128 could rapidly deposit a metered volume of contrast at the same time saline is deposited from hole sets 126 and 130. This "protected" bolus of contrast would then flow from the catheter, surrounded by layers of saline, which would reduce the mixing of contrast with blood, and thereby maintain a relatively high concentration of contrast for vascular imaging purposes. In this case, mixing of contrast and saline would be minimized by the viscosity differences among the several layers of fluid. Alternatively, one or more of the hole sets 126, 128, 130 could slowly deposit contrast, while the remaining holes would deposit saline in order to purposefully mix the fluids and thereby reduce the concentration of the active components of contrast fluid. This mixing works best if blood flow in the vessel is temporarily reduced or stopped by an occlusion means during the deposition of fluid from the hole sets. The balloon 122 is fed by an inflation lumen 124, which is shown as being externally located but could be integrated into the catheter wall or within an internal lumen of the catheter. The balloon 122 may be used to block the blood vessel during injection in order to prevent retrograde flow of injectate. Additionally, the balloon 122 may be used to provide a motive force on a stream of contrast or other injectate in order to overcome the effects of injection into large vessels having a higher blood mass flow rate. The motive force is generated by inflating and deflating the balloon 122 to effectuate a pumping action.

Figure 11:
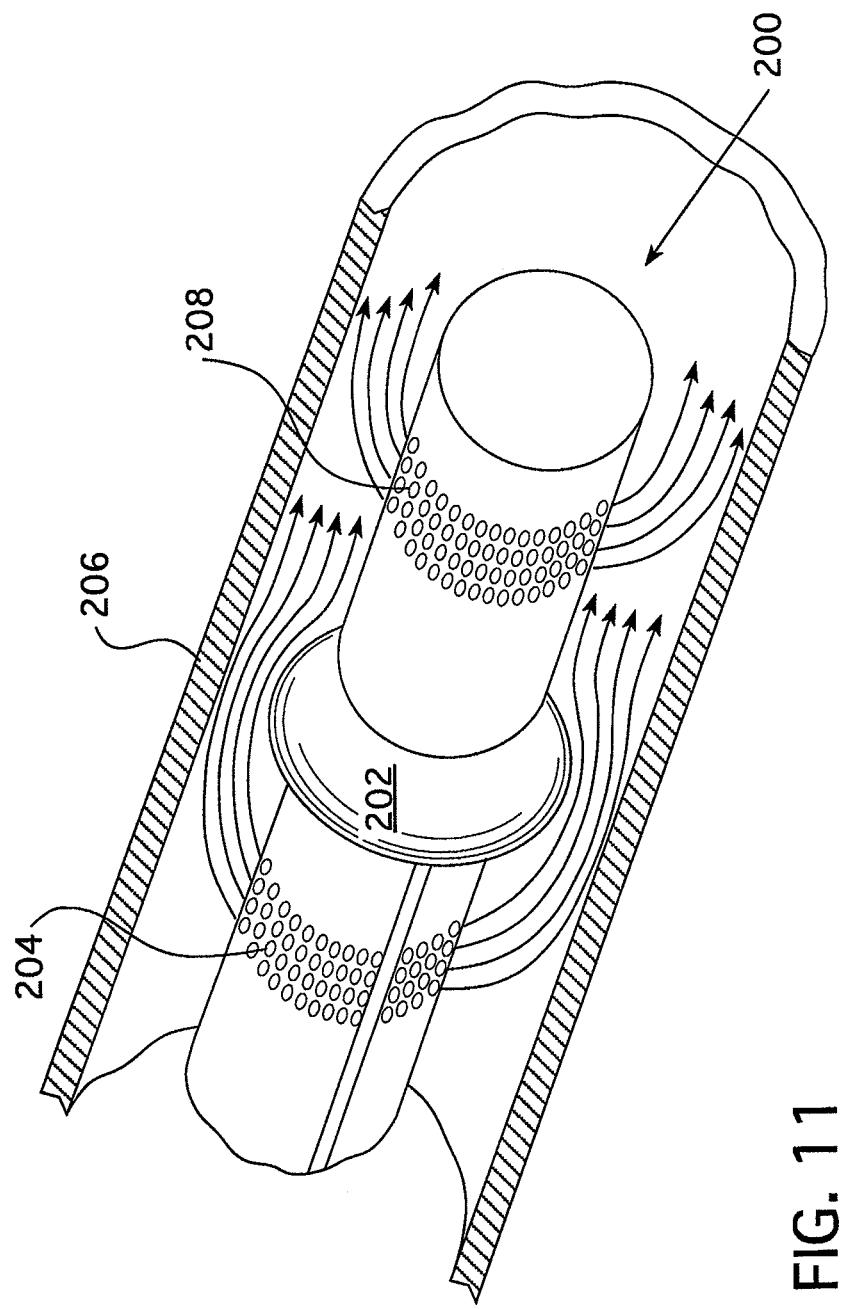
FIG. 11 is a perspective view of an embodiment of a catheter tip.

FIG. 11 shows an embodiment of a catheter tip 200 that also includes an annular structure 202 that creates a nozzle effect. This annular structure 202 could be a balloon, such as that shown in FIG. 10, or could be formed into the catheter wall itself, so long as it did not interfere with catheter navigation. The purpose of the annular structure 202 is to entrain and accelerate the fluid distally, thereby providing forward momentum to the saline solution.

The saline solution is introduced into the blood stream through holes 204 located on a proximal side of the annular structure 202. The shape of the annular structure results in a high velocity flow due to the decreased space between the structure 202 and the native lumen walls 206. The high velocity saline then impacts a second fluid, such as contrast, being introduced into the blood stream from the distal holes 208. The increase in saline speed reduces the chance that the contrast will be refluxed upstream. Rather, the contrast bolus is maintained and pushed downstream. Additionally, under high velocity flow conditions, with an annular structure 202 of the right geometry, boundary layer flow attachment to the surface of the annular structure 202 can occur, e.g., a Coanda-like effect, as described in U.S. Pat. No. 6,129,698, which is incorporated herein by reference.

Proximal End

Figure 12:
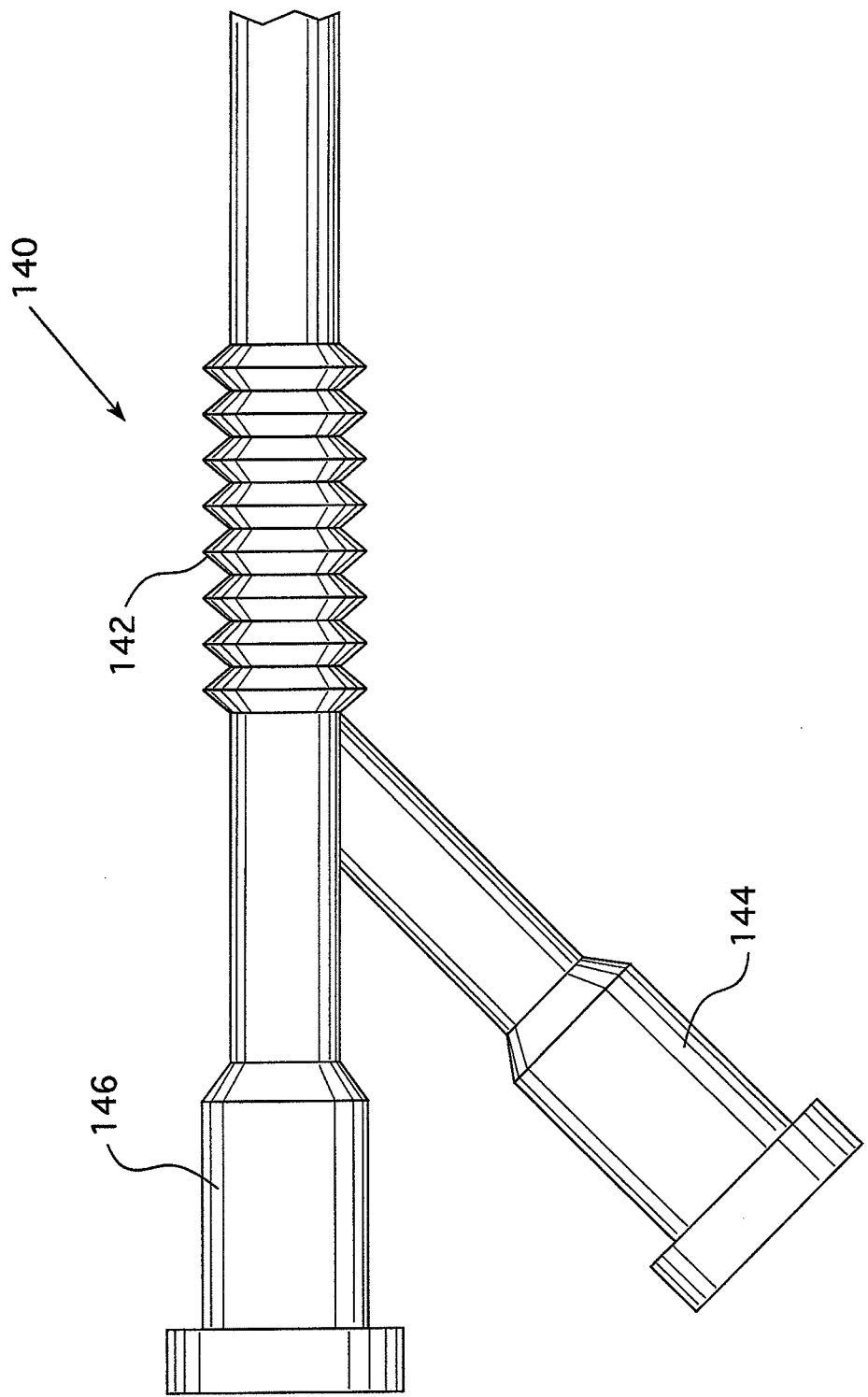
FIG. 12 is a side elevation of a proximal end of a catheter.

FIG. 12 shows an embodiment of a proximal end 140 of a catheter, such as any of those described herein. The proximal end 140 includes baffles 142 that can be inflated or deflated using a baffle inflation port 144. A main injection port 146 provides fluid access to the main lumens of the catheter. The baffles 142 increase the maneuverability of the device by allowing very small incremental advances of the catheter for precise positioning. Injecting fluid through the baffle inflation port 144 causes the baffles 142 to elongate longitudinally.

Operation

Figure 13A:
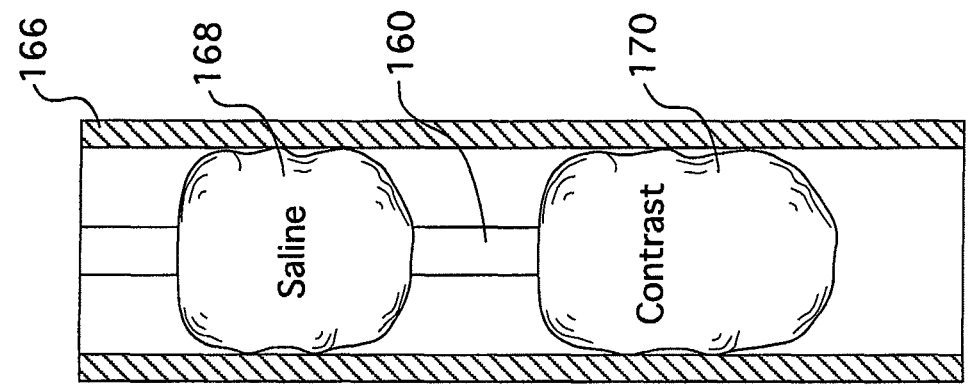
FIG. 13a is a diagram of an embodiment of a catheter tip in a body lumen.

In operation, and using the embodiment of FIG. 1 as an example only, contrast agent may be injected into the blood stream via the distal hole set 22 concurrently with non-contrasting fluid, such as saline, through the proximal hole set 20. If the proximal, saline injection is performed at the correct volume and flow rate, a high pressure bolus of saline in the blood stream blocks the contrast agent being emitted from the distal hole set 22 from flowing in a retrograde direction. Hence, the saline bolus acts as a virtual balloon or flow-blocking mechanism, sharpening the definition of the contrast agent bolus. When imaging the heart and injecting contrast into the venous side, the proximal pressure of the saline forces the contrast agent into the right atrium from the superior and inferior vena cava. FIGS. 13a,b and 14a,b compare the injections of a single bolus cloud and a double bolus cloud.

Figure 13B:
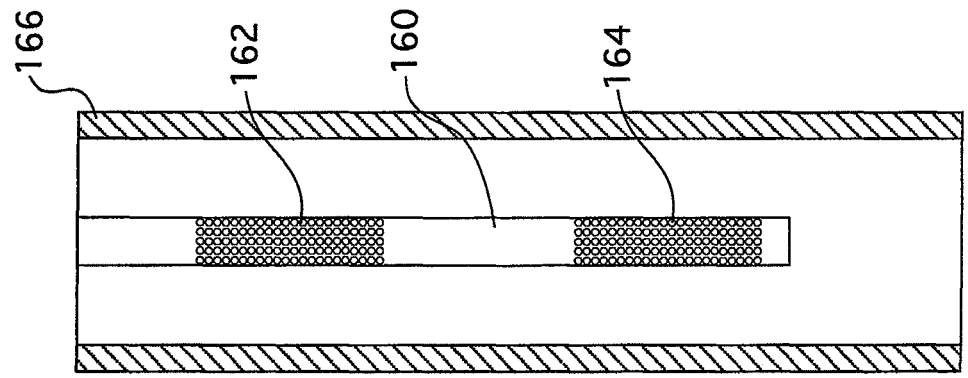
FIG. 13b is a diagram of the catheter tip of FIG. 13a injecting contrast agent into a body lumen.

FIG. 13a shows a single lumen catheter 150 with a single hole set 152 in a body lumen 154. FIG. 13b shows a contrast bolus 156 being emitted from the catheter 150. The bolus 156 is able to travel in both directions, as indicated by the bidirectional flow arrow 158.

Figure 14A:
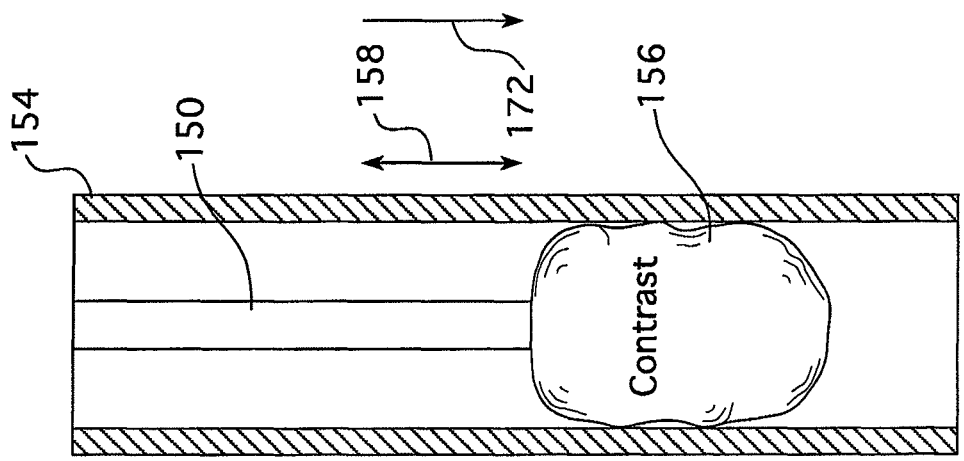
FIG. 14a is a diagram of an embodiment of a catheter tip in a body lumen.
Figure 14B:
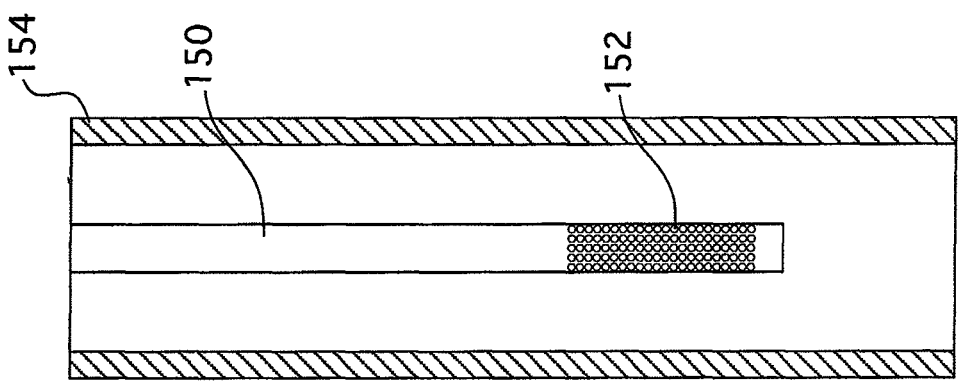
FIG. 14b is a diagram of the catheter tip of FIG. 14a injecting saline and contrast agent into a body lumen.

FIG. 14a shows a dual lumen catheter 160 with a proximal hole set 162 and a distal hole set 164 in a body lumen 166. FIG. 14b shows a saline bolus 168 and a contrast bolus 170 being emitted from the catheter 160. The contrast bolus 170 is able to travel in only one direction, as indicated by the flow arrow 172, due to the presence of the saline bolus 168.

Imaging the heart can be further enhanced using two sets of simultaneous saline/contrast agent injections. The first set of simultaneous injections can be described as a levo contrast phase whereby the simultaneous injections are made and then a pause before a second set of simultaneous injections is timed to allow the agent to travel into the left side of the heart. At this point, or slightly prior thereto, a second set of simultaneous contrast agent/saline injections is performed such that both sides of the heart are filled with contrast agent at the same time, thereby allowing excellent imaging of the entire heart. Because a pause in the injection sequence allows opacification of both sides of the heart to occur simultaneously, less contrast agent is used than would be the case if the contrast agent were to be injected continuously until the heart was flooded with the agent.

The bolus of agent may be "pumped" in order to overcome a high lumen pressure in the venous lumen. Modulation of the flow rate through the proximal hole set alters the pressure through the proximal hole set, thereby altering the pressure and size of the saline bolus. When the pressure of the saline bolus exceeds the pressure of the agent bolus distal thereto, and the pressure of the venous lumen, the saline bolus effectively pushes the agent bolus in a distal, or antegrade direction. This pumping effect may be enhanced by using an annular balloon, like the annular balloon 122 shown in FIG. 10 and described above.

What is claimed is:

1. A catheter for introducing more than one fluid into a fluid stream, the more than one fluid comprising a first fluid and a second fluid, wherein the catheter comprises:
    (a) a catheter body comprising a distal tip defining a distal end, wherein the catheter body defines at least a first lumen and a second lumen;
    (b) a first set of holes in said distal tip leading to the first lumen to deliver the first fluid into the fluid stream, said first set of holes proximal of said distal end;
    (c) a second set of holes in said distal tip leading to the second lumen to deliver the second fluid into the fluid stream, said second set of holes proximal of said distal end;
    (d) an annular structure on an outside surface of said distal tip and located between said first set of holes and said second set of holes; and
    (e) wherein said first set of holes is distal of said second set of holes and the first fluid has a higher viscosity than the second fluid, such that delivery of metered volumes of the first fluid and the second fluid maintains a bolus of the first fluid by minimizing mixing of the first fluid and the second fluid due to the viscosity differences.

2. The catheter of claim 1 wherein said annular structure comprises a balloon.

3. The catheter of claim 1 wherein said annular structure comprises an occlusion device.

4. The catheter of claim 1 wherein said first lumen and said second lumen each have a semi-circular cross-section.

5. The catheter of claim 1 wherein said first lumen and said second lumen are concentric.

6. The catheter of claim 1 wherein the first fluid comprises a contrast agent and the second fluid comprises a diluent.

7. A catheter for introducing more than one fluid into a fluid stream, the more than one fluid comprising a first fluid and a second fluid, wherein the catheter comprises:
    (a) a catheter body comprising a distal tip defining a distal end, wherein the catheter body defines at least a first lumen and a second lumen;
    (b) a first set of holes in said distal tip leading to the first lumen to deliver the first fluid into the fluid stream, said first set of holes proximal of said distal end;
    (c) a second set of holes in said distal tip leading to the second lumen to deliver the second fluid into the fluid stream, said second set of holes proximal of said distal end;
    (d) an annular structure on an outside surface of said distal tip and located proximal of at least one of said first set of holes and said second set of holes; and
    (e) wherein said first set of holes is distal of said second set of holes and wherein said annular structure defines a non-occluding annular orifice thereabout with a body vessel into which it is placed, the body vessel containing bodily fluid flowing downstream therein and passing the annular structure via the non-occluding annular orifice.

8. The catheter of claim 7 wherein said annular structure comprises a balloon.

9. The catheter of claim 7 wherein said annular structure is located proximal of said first and said second sets of holes.

10. The catheter of claim 7 wherein said annular structure comprises an occlusion device.

11. The catheter of claim 7 wherein said first lumen and said second lumen each have a semi-circular cross-section.

12. The catheter of claim 7 wherein said first lumen and said second lumen are concentric.

13. The catheter of claim 7 wherein the first fluid comprises a contrast agent and the second fluid comprises a diluent.

14. A catheter for introducing more than one fluid into a fluid stream, the more than one fluid comprising a first fluid and a second fluid, wherein the catheter comprises:
    (a) a catheter body comprising a distal tip defining a distal end, wherein the catheter body defines at least a first lumen and a second lumen;
    (b) a first set of holes in said distal tip leading to the first lumen to deliver the first fluid into the fluid stream, said first set of holes proximal of said distal end;
    (c) a second set of holes in said distal tip leading to the second lumen to deliver the second fluid into the fluid stream, said second set of holes proximal of said distal end;
    (d) an annular structure on an outside surface of said distal tip and located proximal of at least one of said first set of holes and said second set of holes; and
    (e) wherein said first set of holes is distal of said second set of holes and wherein said annular structure is shaped to cause boundary layer attachment thereto of the second fluid emanating from said second set of holes and thereby provide downstream momentum to the second fluid so as to prevent upstream flow of the first fluid emanating from said first set of holes and to maintain a bolus of the first fluid.

15. The catheter of claim 14 wherein velocity of the second fluid emanating from said second set of holes is controlled by varying a cross-sectional area of said annular structure.

16. The catheter of claim 14 wherein said annular structure comprises a balloon.

17. The catheter of claim 14 wherein said annular structure comprises an occlusion device.

18. The catheter of claim 14 wherein said first lumen and said second lumen each have a semi-circular cross-section.

19. The catheter of claim 14 wherein said first lumen and said second lumen are concentric.

20. The catheter of claim 14 wherein the first fluid comprises a contrast agent and the second fluid comprises a diluent.

* * * * *

UNITED STATES PATENT AND TRADEMARK OFFICE
CERTIFICATE OF CORRECTION

PATENT NO. : 8,702,649 B2  Page 1 of 1
APPLICATION NO. : 12/515981
DATED : April 22, 2014
INVENTOR(S) : Schwartz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1262 days.

Signed and Sealed this
Twenty-ninth Day of September, 2015

Michelle K. Lee
*Director of the United States Patent and Trademark Office*